United States Patent
Flohr et al.

(10) Patent No.: US 6,792,068 B1
(45) Date of Patent: Sep. 14, 2004

(54) COMPUTED TOMOGRAPHY DEVICE WITH A MULTI-LINE DETECTOR SYSTEM

(75) Inventors: Thomas Flohr, Uehlfeld (DE); Bernd Ohnesorge, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/048,052

(22) PCT Filed: Jul. 25, 2000

(86) PCT No.: PCT/DE00/02438

§ 371 (c)(1),
(2), (4) Date: Aug. 6, 2002

(87) PCT Pub. No.: WO01/06930

PCT Pub. Date: Feb. 1, 2001

(30) Foreign Application Priority Data

Jul. 27, 1999 (DE) .......................... 199 35 093

(51) Int. Cl.[7] ............................... H05G 1/60
(52) U.S. Cl. ........................ 378/19; 378/98.8
(58) Field of Search ................ 378/19, 98.8, 4, 378/207; 250/370.09, 367

(56) References Cited

U.S. PATENT DOCUMENTS

| | | | |
|---|---|---|---|
| 4,965,726 A | * | 10/1990 | Heuscher et al. ............. 378/19 |
| 5,355,309 A | | 10/1994 | Eberhard et al. |
| 5,430,784 A | * | 7/1995 | Ribner et al. .................. 378/19 |
| 5,974,109 A | | 10/1999 | Hsieh |
| 6,157,696 A | * | 12/2000 | Saito et al. .................... 378/19 |
| 6,188,745 B1 | * | 2/2001 | Gordon ......................... 378/19 |
| 6,215,848 B1 | * | 4/2001 | Linders et al. ........... 378/98.12 |
| 6,243,438 B1 | * | 6/2001 | Nahaliel et al. .............. 378/19 |
| 6,259,766 B1 | * | 7/2001 | Cuppen ........................ 378/19 |
| 6,400,793 B2 | * | 6/2002 | Doubrava et al. ............ 378/19 |
| 6,535,571 B2 | * | 3/2003 | Von Der Haar ................ 378/19 |

FOREIGN PATENT DOCUMENTS

| | | |
|---|---|---|
| DE | 195 02 574 | 8/1996 |
| GB | 2 005 955 | 4/1979 |
| GB | 2 074 415 | 10/1981 |
| GB | 2 088 670 | 6/1982 |

* cited by examiner

Primary Examiner—Craig E. Church
Assistant Examiner—Hoon Song
(74) Attorney, Agent, or Firm—Schiff Hardin LLP

(57) ABSTRACT

In a CT device with a multi-line detector system, different columns of the detector system can be connected to different numbers of electronic elements in order to read the signals generated in the detector elements. Thus, by using the detector systems, regions of the object to be examined can be scanned with a high resolution, and other regions can be scanned with a lower resolution. A high resolution in regions can therefore be achieved with a simplified and less expensive detector system, which generates a comparatively low data rate and amount of data.

7 Claims, 2 Drawing Sheets

COMPUTED TOMOGRAPHY DEVICE WITH A MULTI-LINE DETECTOR SYSTEM

This application is a 371 of PCT/DE00/02438 filed Jul. 25, 2000.

BACKGROUND OF THE INVENTION

1. Field of the Invention

The invention relates to a CT (computed tomography) device of the type having a radiation source which, in order to scan an object to be examined, can be displaced relative to a system axis and emits a beam of radiation, which strikes a detector system formed by an array of lines and columns of detector elements, the measured values obtained in this way being associated with one of a large number of projection angles and being supplied to a computer, which uses them to calculate images of the object to be examined, the signals generated in the detector elements by radiation being supplied to electronic elements to be read and amplified, the number of detector elements of the detector system exceeding the number of electronic elements.

2. Description of the Prior Art

CT devices are known which have a radiation source, for example an X-ray tube, which directs a collimated, pyramidal beam of radiation through the object to be examined, for example a patient, onto a detector system formed by a number of detector elements. The radiation source and, depending on the design of the CT device, the detector system also are mounted to a gantry, which rotates around the object to be examined. A mounting device for the object to be examined can be displaced or moved along the system axis relative to the gantry. The position from which the radiation beam passes through the object to be examined, and the angle at which the beam of radiation passes through the object to be examined, are varied continually as a result of the rotation of the gantry. Each detector element in the detector system that is affected by the radiation produces a signal which constitutes a measure of the overall transparency of the object to be examined for the radiation originating from the radiation source on its path to the detector system. The set of output signals from the detector elements of the detector system, which is obtained for a specific position of the radiation source, is referred to as a projection. A scan is formed by a set of projections, which have been obtained at various positions of the gantry and/or various positions of the mounting device. During one scan, the CT device assumes a large number of projections, in order to be able to build up a two-dimensional sectional image of a layer of the object to be examined. With a detector system constructed from an array of lines and columns of detector elements, a number of layers can be recorded at the same time.

German OS 195 02 574 discloses a CT device of the type mentioned in the introduction having a multi-line detector system, in which, in order to save cost and in order to limit the data rates, the read electronics connected downstream of the detector elements does not have an electronic element for each detector element. Instead, the number of detector lines exceeds the number of lines of electronic elements. Each line of electronic elements can be associated with a number of detector lines via multiplexers and summers.

In this known CT device, a disadvantage is that, as a result of connecting adjacent detector lines together, the thickness of the layers recorded increases, and therefore the resolution in the z-direction is decreased. Another disadvantage is that each detector line is not connected to a line of electronic elements, and therefore it is not possible for the entire detector width in the z-direction to be used for data acquisition.

German OS 198 35 873 discloses a CT device of the type mentioned in the introduction, in which the number of detector elements exceeds the number of electronic elements and, therefore, region by region, a number of detector elements of a detector line are coupled, i.e., are connected to one electronic element, with the coupling of detector elements being omitted in the central region of the detector lines.

SUMMARY OF THE INVENTION

An object of the present invention is to provide a CT device of the type mentioned in the introduction wherein, in spite of a reduced number of electronic elements, as compared with the number of detector elements, a high resolution can be achieved with the detector system and, nevertheless, a high number of individual layers can be recorded at the same time.

According to the invention, this object is achieved by a CT device having a radiation source which, in order to scan an object to be examined, can be displaced relative to a system axis and emits a radiation beam, which strikes a detector system formed by an array of lines and columns of detector elements, the measured values obtained in this way being associated with one of a large number of projection angles and being supplied to a computer, which uses them to calculate images of the object to be examined, signals generated in the detector elements by radiation being supplied to electronic elements to be read and amplified, the number of detector elements of the detector system exceeding the number of electronic elements, and wherein a region of detector columns including at least one detector column can be connected to a larger number of electronic elements, in order to read out the detector elements from this region, than is a different region having the same number of detector columns.

The CT device according to the invention therefore not only has the advantage that the detector system can be implemented more simply and less expensively by means of the number of electronic elements being reduced with respect to the number of detector elements, but also, therefore, region by region a larger number of layers can be recorded at the same time than in the case of detector systems with a reduced number of electronic elements according to the prior art.

Whereas in known CT devices, adjacent detector elements can if required be connected together line by line, and each detector column is associated with a permanently predefined number of electronic elements, the detector system according to the invention can be divided into regions with a different resolution both in the z-direction and in the φ-direction. To this end, different detector columns of the detector system according to the invention can be connected to different numbers of electronic elements. If, for example, a CT device according to the prior art has an 8-line detector system with four lines of electronic elements, then each detector column of the detector system is connected to a maximum of four electronic elements compared to this, a CT device according to the invention, likewise having an 8-line detector system, permits specific detector columns to be connected, for example, to six electronic elements and other detector columns to be connected only to two electronic elements per detector column. A suitable arrangement of multiplexers and summation elements between the detector elements and the electronic elements permits a largely random interconnection of detector elements and the assignment of individual detector elements or interconnected detector elements to individual electronic elements.

A region of the detector system of the CT device according to the invention whose detector columns are assigned an increased number of electronic elements can, for example, be the especially relevant central region of the detector system. Outside the central region, correspondingly fewer measured values are formed as a result of detector elements being combined or not being taken into account. Given the same overall z-length of the collimated layer over the entire detector, many thin individual layers are in this way obtained in one region, but a few wide individual layers in another region. Therefore, in the one region, the number of effective lines, and therefore the resolution in the z-direction, is increased, without additional electronic elements being required for this purpose. In addition, the data rates and amounts of data that can be generated by the detector system do not change with respect to a known detector system having a reduced number of electronic elements.

In the CT device according to the invention, the object to be examined can fill the entire measurement field, as hitherto. The object to be examined is merely scanned with a higher resolution in one region than in another region. If the object to be examined fills only a portion of the measurement field as, for example, in the case of examinations of internal organs, the head or the extremities of a patient, then the electronic elements of the detector system according to the invention can be connected to the detector elements so that all the electronic elements are assigned to the relevant region of the detector system, and the edge regions of the detector system, which cannot contribute any measured values to the objects to be displayed, are not assigned any electronic elements. As a result of the simultaneous recording of many thin individual layers, this also leads to an improved resolution with a simultaneous saving in time and costs.

In an embodiment of the invention missing measured values from a region with low resolution are interpolated from the measured values obtained from this region, or missing measured values from a region with a low resolution to be extrapolated from measured values from a region with a high resolution. The values formed in this way, together with the measured values, can then be supplied to a conventional CT multi-line image reconstruction.

Therefore, in this variant, known software can be used in the image reconstruction, which limits the effort and the costs which have to be applied in connection with the creation of the software for a CT device.

Larger volumes of an object to be examined are normally registered by means of sequential scanning or spiral scanning. The CT device according to the invention can advantageously be used for both types of scan.

In the case of sequential scanning, the data are recorded during a rotational movement of the gantry, while the object to be examined is located in a fixed position, and therefore a specific number of planar layers are scanned. In order to scan the following layers, the object to be examined is moved into a new position relative to the gantry. This procedure is continued until the volume defined before the examination has been scanned.

In the case of spiral scanning, the gantry with the X-ray radiation source rotates around the object to be examined, while the mounting table and the gantry are displaced continuously relative to each other along a system axis. The radiation source therefore describes a spiral path in relation to the object to be examined, until the volume defined before the examination has been scanned. Images of individual layers are then calculated from the spiral data obtained in this way.

The detector system of the CT device according to the invention may be constructed in a simple and cost-effective way as a modification (retrofit) of conventional detector systems. By means of the arrangement of summation elements and multiplexers between the detector elements and the electronic elements, and the corresponding wiring, the electronic elements are supplied the charges generated by absorption of radiation in the detector elements, to be read and amplified.

In a preferred embodiment of the detector system according to the invention, the length of the detector elements is different in the direction of the system axis (z-direction). In addition to the advantages already mentioned of a detector system according to the invention, this provides the further advantage that, region by region, by means of appropriate interconnection of adjacent detector elements, additional operating modes are therefore possible with this detector system. For example, in the case of an 8-line detector system having the following detector elements which are not equidistant in the z-direction:

5 mm-2.5 mm-1.5 mm-1 mm-1 mm-1.5 mm-2.5 mm-5 mm by means of partial insertion of outer detector elements and combination, the following modes can additionally be realized region by region, in which six layers are scanned:

Mode 1: 2.5 mm-2.5 mm-2.5 mm-2.5 mm-2.5 mm

Mode 2: 1 mm-1.5 mm-1 mm-1 mm-1.5 mm-1 mm

DESCRIPTION OF THE PREFERRED EMBODIMENTS

Figure 1:
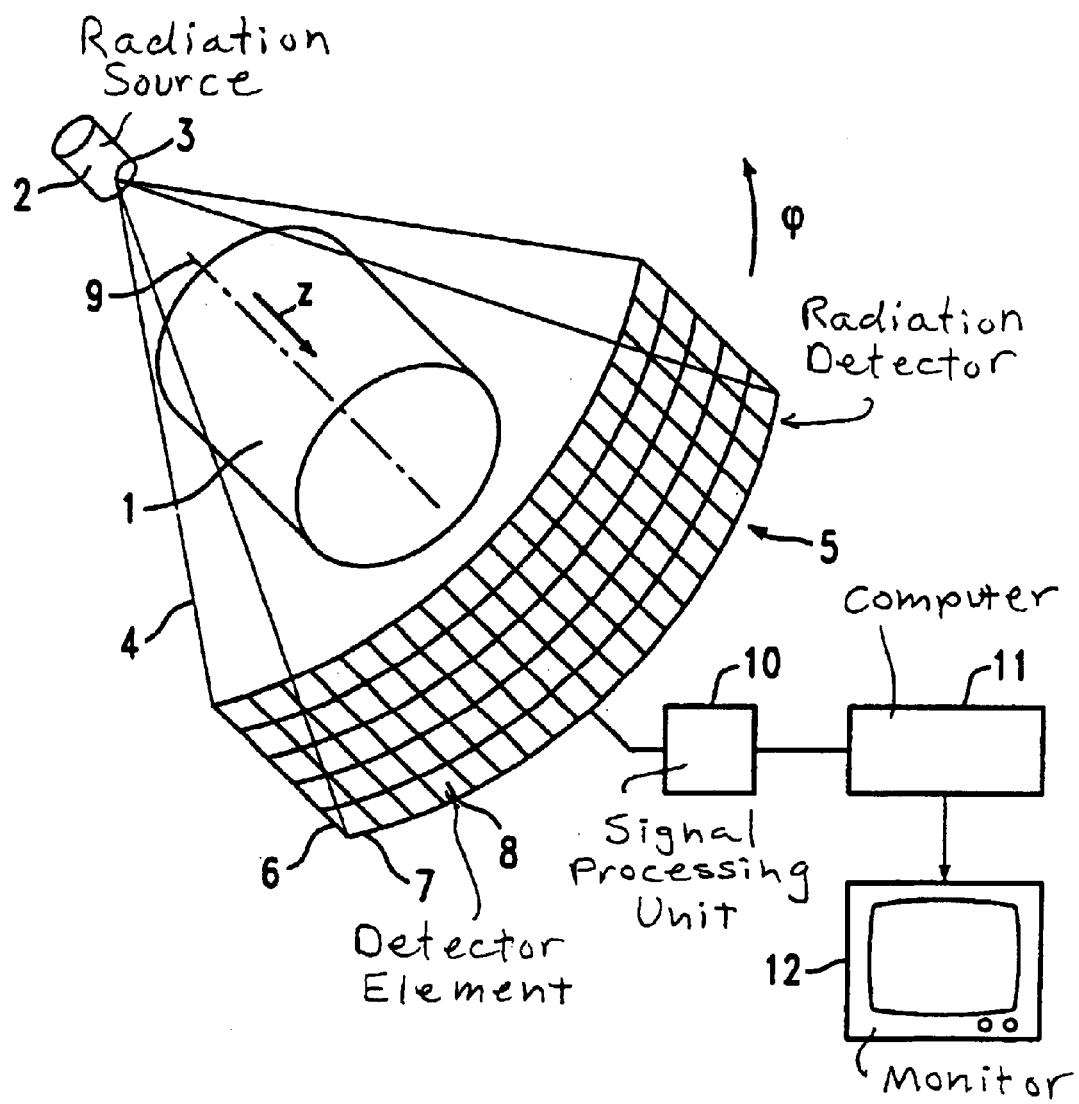
FIG. 1 is a block diagram showing the basic components of an X-ray computed tomography device constructed and operating in accordance with the present invention.

FIG. 1 shows a CT device which is provided for scanning an object 1 to be examined and which has a radiation source 2, for example an X-ray tube, with a focus 3 from which a pyramidal beam 4 of radiation collimated by a radiation diaphragm (not illustrated) originates, passes through the object 1 to be examined, for example a patient, and strikes a detector system 5.

The latter has an array of parallel lines 6 and parallel columns 7 of detector elements 8. The radiation source 2 and the detector system 5 form a measuring system, which can be displaced in the φ-direction around a system axis 9 and can be displaced along the system axis relative to the object 1 to be examined, so that the object 1 to be examined is irradiated at various projection angles and various z-positions along the system axis 9. From the output signals which occur in the process from the detector elements 8 of the detector system 5, a signal processing unit 10 forms measured values, which are supplied to a computer 11, which calculates an image of the object 1 to be examined, which is reproduced on a monitor 12.

Figure 2:
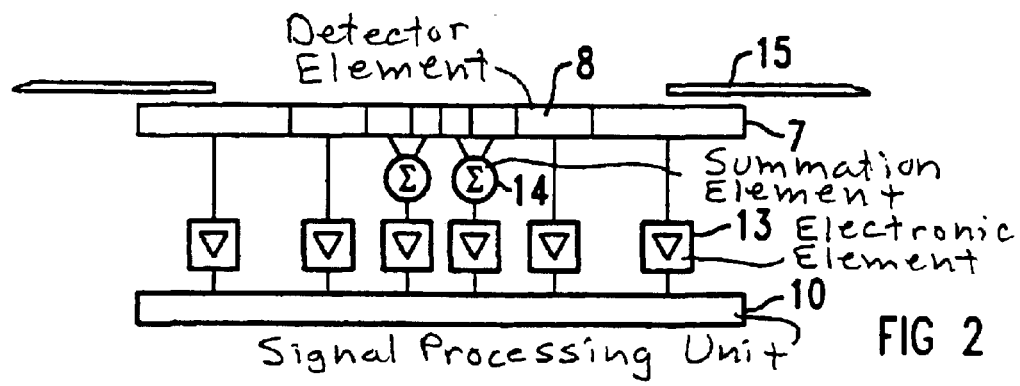
FIG. 2 shows one column in a central region of the detector system of the computed tomography device of FIG. 1, showing how the electronic components are associated with the detector elements of the column.
Figure 3:
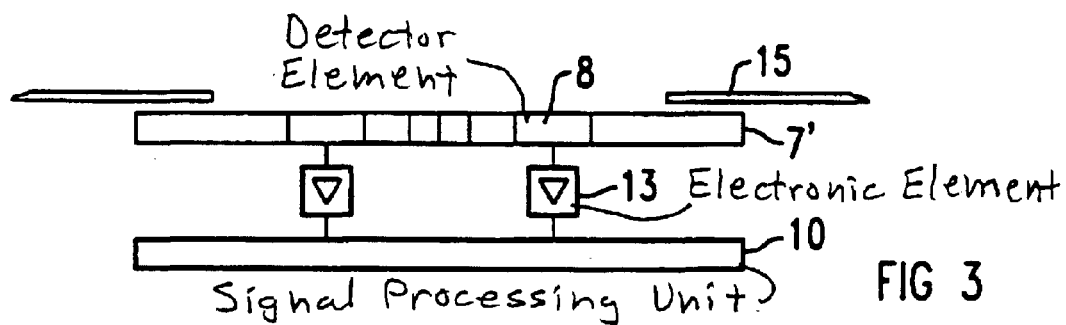
FIG. 3 shows one column in a outer region of the detector system of the computed tomography device of FIG. 1, showing how the electronic components are associated with the detector elements of the column.
Figure 4:
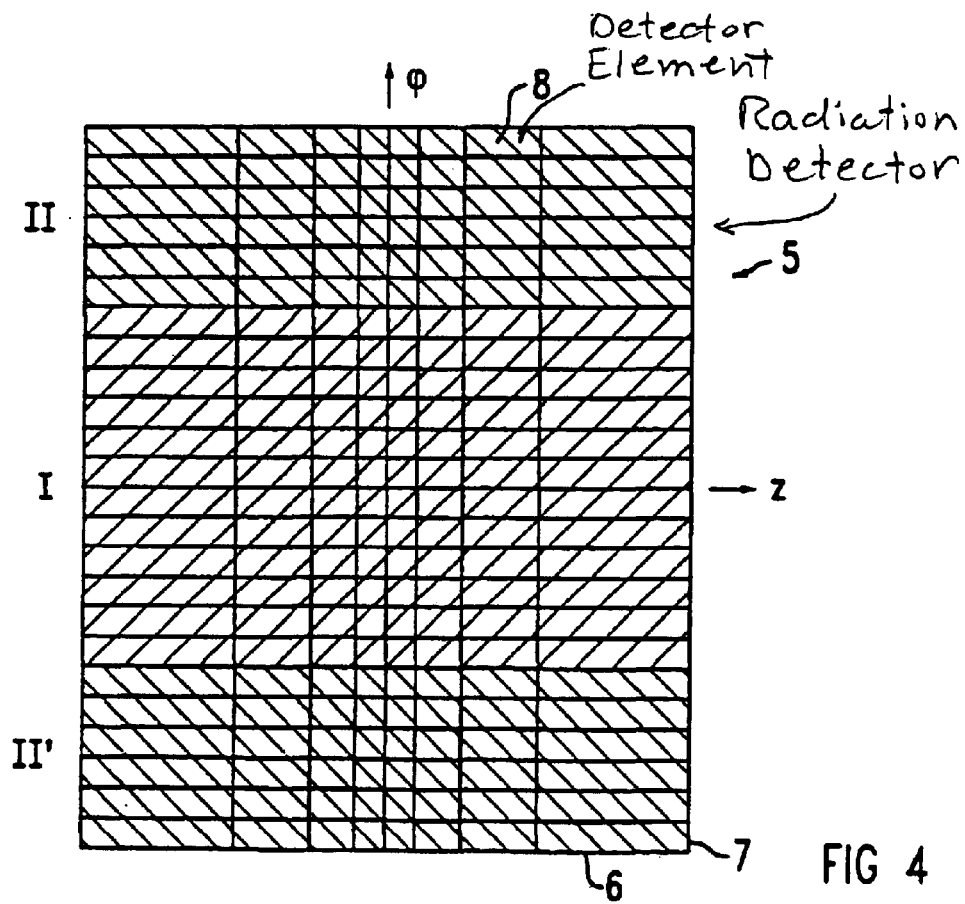
FIG. 4 is a plan view of the detector system of the computed tomography device according to FIG. 1.

In FIG. 1, the detector system 5 is shown only schematically with a number of lines and columns that differs from FIGS. 2 to 4. FIGS. 2 to 4 show that, in the case of the exemplary embodiment described, the detector system has eight lines 6 and twenty-four columns 7, the length of the detector elements 8 in the z-direction, that is to say in the direction of the system axis 9, not being the same for all lines. By means of appropriate insertion and combination of detector lines 6, this geometry is very flexible in the selection of the layer thicknesses to be scanned of the object to be examined. In the middle, each column 7 of the detector system 5 is assigned four electronic elements 13 to read out and amplify the charges generated in the detector elements 8 by the absorption of X radiation. The association between an electronic element 13 and one or more detector elements 8 is carried out via summation elements 14 and multiplexers (not illustrated). The signals registered by the electronic elements 13 are supplied to a signal processing unit 10 for further processing.

As FIG. 2 reveals, the eight detector elements 8 of the detector column 7 illustrated, which, according to FIG. 4, lies in the central region of the detector system 5 in the φ-direction, are connected to six electronic elements 13, of the central four detector elements, in each case two, combined via a summation element 14, being connected to one electronic element 13. Signals from all the detector elements in this detector column are thus registered and supplied to the signal processing unit 10.

In order on average to achieve the assignment of four electronic elements per detector column, eight detector elements from another detector column 7', shown in FIG. 3, are assigned only two electronic elements 13. The detector column 7' in this case lies in the outer region of the detector system 5 in the φ-direction, according to FIG. 4.

Measured values which are missing as compared with the detector column 7 according to FIG. 2 are interpolated from the measured values obtained with the detector column 7' and/or extrapolated from the measured values from adjacent detector columns by means of the computer 11. Therefore, for further signal processing, recourse can be made to image reconstruction algorithms already implemented.

FIG. 4 shows the division of the exemplary detector system 5 into eight lines 6 and twenty-four columns 7 of detector elements 8 in each case. If, for example, only a section of the object 1 to be examined is to be examined, for example in order to image internal organs, the head or the extremities of a patient, then given appropriate positioning of the object 1 to be examined in the CT device, one subregion of the detector system 5 is particularly relevant for registering measured values. In the example according to FIG. 4, this is assumed to be the central region I of the detector system 5, containing twelve columns 7 of detector elements 8. In order to increase the resolution in this particularly relevant measurement region, the detector columns 7 according to FIG. 2 are each connected to six electrical elements 13. In order to compensate, the columns 7 from the outer regions II and II' of the detector system 5, of less interest for obtaining measured data, are each connected only to two electronic elements 13. Missing measured values are interpolated by the computer 11 from the existing measured values from the relevant regions, or are extrapolated from the measured values from region I. The data obtained in this way are then processed by the computer 11 in accordance with the usual image reconstruction methods.

As can also be seen from FIGS. 2 to 4, in this exemplary embodiment the detector elements of a detector column have different longitudinal extents in the z-direction. In the example, these are:

5 mm-2.5 mm-1.5 mm-1 mm-1 mm-1.5 mm-2.5 mm-5 mm

Then, by combining the 1.5 mm elements with the 1 mm elements by means of the summation elements 14 in the way illustrated in FIG. 2, and by inserting the outer 5 mm elements by means of the beam apertures 15, with this detector system the following mode with 6 lines is also possible, for example for the especially relevant region I that can be seen from FIG. 4:

2.5 mm-2.5 mm-2.5 mm-2.5 mm-2.5 mm

The invention is not restricted to the exemplary embodiment illustrated, but can be used for multi-line detector systems with any desired number of detector lines and detector columns. In addition, the length of the detector elements in the z-direction can deviate from the exemplary embodiment illustrated within the context of the invention. In particular, the invention also covers detector systems with the same longitudinal extent of the detector elements in the z-direction.

The exemplary embodiment described above is a CT device of the third generation, i.e. the X-ray source and the detector rotate jointly about the system axis during the generation of an image. However, the invention can also be used in CT devices of the fourth generation, in which only the X-ray source rotates and co-operates with a stationary detector ring.

The exemplary embodiment described above relates to the medical application of a CT device according to the invention. However, the invention can also be applied outside medicine, for example in luggage testing or in material examination.

Although modifications and changes may be suggested by those skilled in the art, it is the intention of the inventors to embody within the patent warranted hereon all changes and modifications as reasonably and properly come within the scope of their contribution to the art.

We claim:

1. A computed tomography device comprising:
    a radiation source which emits a radiation beam from a focus, at least said focus being displaceable relative to a system axis to scan an examination subject with said radiation beam from a plurality of projection angles;
    a radiation detector on which said radiation beam is incident after passing through said examination subject, said radiation detector being formed by a plurality of detector elements in rows proceeding substantially perpendicularly to said system axis and columns proceeding substantially parallel to said system axis, each of said detector elements generating an electrical signal corresponding to radiation from said radiation beam incident thereon;
    a plurality of electronic elements for reading out said electrical signals from said detector elements, to generate measured values;
    the detector elements in a first region of said columns of said radiation detector, including at least one entire column, being connected to a larger number of said electronic elements than the detector elements in a second region of said columns of said radiation detector comprising a same number of said columns; and a computer supplied with said measured values for reconstructing an image of said examination subject therefrom.

2. A computed tomography device as claimed in claim 1 wherein the detector elements in at least one of said columns are not connected to any of said electronic elements.

3. A computed tomography device as claimed in claim 1 wherein said computer generates additional measured values from said second region by interpolation of the measured values from the electronic elements connected to the detector elements in said second region.

4. A computed tomography device as claimed in claim 1 wherein said computer generates additional measured values from said second region by extrapolation from the measured values from the electronic elements connected to the detector elements in said first region.

5. A computed tomography device as claimed in claim 1 further comprising a support arrangement adapted to receive said examination subject thereon and a displacement arrangement for producing relative displacement between said radiation beam and said support mechanism along said system axis, with said projections being obtained at successive positions along said system axis.

6. A computed tomography device as claimed in claim 1 wherein said detector elements are detector elements which generate said electrical signals by producing electrical charges due to absorption of said radiation.

7. A computed tomography device as claimed in claim 1 wherein the detector elements in one of said rows have a first length in a direction along said system axis and wherein the detector elements in another of said rows have a second length in said direction along said system axis, said first and second lengths being different.

* * * * *